United States Patent [19]

Mee

[11] Patent Number: 5,679,795
[45] Date of Patent: Oct. 21, 1997

[54] METHOD OF SYNTHESIZING DYES AND PRECURSOR COMPOUNDS THEREFOR

[75] Inventor: John David Mee, Rochester, N.Y.

[73] Assignee: Eastman Kodak Company, Rochester, N.Y.

[21] Appl. No.: 476,541

[22] Filed: Jun. 7, 1995

Related U.S. Application Data

[63] Continuation-in-part of Ser. No. 395,265, Feb. 28, 1995, abandoned.

[51] Int. Cl.$^6$ .................... C07D 277/24; C07D 277/26; C07D 277/28
[52] U.S. Cl. .................... 548/182; 548/189; 548/187
[58] Field of Search .................... 548/182, 187, 548/189

[56] References Cited

U.S. PATENT DOCUMENTS

| | | | |
|---|---|---|---|
| 2,395,879 | 3/1946 | Kendall et al. | 260/240 |
| 2,504,615 | 4/1950 | Anish | 95/7 |
| 2,575,018 | 11/1951 | Keyes et al. | 260/240 |
| 3,384,486 | 5/1968 | Taber et al. | 96/74 |
| 3,385,707 | 5/1968 | Riester et al. | 96/102 |
| 3,436,397 | 4/1969 | Davis et al. | 260/306.7 |
| 3,436,398 | 4/1969 | Davis et al. | 260/306.7 |
| 3,682,640 | 8/1972 | Shiba et al. | 96/99 |
| 3,877,937 | 4/1975 | Keller et al. | 96/1.6 |
| 3,912,507 | 10/1975 | Keller et al. | 96/1.5 |
| 4,030,925 | 6/1977 | Leone et al. | 96/73 |
| 4,031,127 | 6/1977 | Leone et al. | 260/465 |
| 4,278,748 | 7/1981 | Sidhu et al. | 430/212 |
| 4,323,643 | 4/1982 | Mifune et al. | 430/441 |
| 4,552,828 | 11/1985 | Toya et al. | 430/217 |
| 4,664,694 | 5/1987 | Brouwer et al. | 71/90 |
| 4,885,369 | 12/1989 | Uryu et al. | 548/183 |
| 4,975,354 | 12/1990 | Machonkin et al. | 430/264 |
| 5,116,722 | 5/1992 | Callant et al. | 430/363 |

FOREIGN PATENT DOCUMENTS

| | | |
|---|---|---|
| 0 427 892 | 5/1991 | European Pat. Off. |
| 0 540 295 | 5/1993 | European Pat. Off. |
| 2102176 | 7/1971 | Germany. |
| 5-224330 | 9/1993 | Japan. |
| 212749 | 2/1968 | U.S.S.R. |
| 489335 | 7/1938 | United Kingdom. |
| 503478 | 4/1939 | United Kingdom. |
| 666226 | 2/1952 | United Kingdom. |

OTHER PUBLICATIONS

Doelling et al., Synthesis, 7, 621–3 (1990).
Mohareb et al., Liebigs Ann. Chem., 11, 1143–46 (1990). 1991.
Mohareb, et al., Tetrahedron, 50(19), 5807–20 (1994).
Peseke, et al., Pharmazie, 41, 548–50, (1986).
El-Shafei, et al., Phos. Sul. Sil., 73, 15–25 (1992).
Ram et al., Phos. Sul. Sil., 88, 155–61 (1994).
Liebigs Annalen Der Chemie, vol. 1992, No. 4, Apr. 1992, Weinheim DE, pp. 387–393, by Rudorf et al, "Ambidoselective Dithiocarboxylation and Thiocarbamoylation of B–Keto Enolates".
Indian Journal of Chemistry, vol. 29, No. 12, Dec. 1990, New Delhi, pp. 1146–1153, by M. R. Mehta; J. P. Trivedi, "Synthesis of 2,3-disubstituted-4-thiazolidinones and 3,5-diaminothiophene-2-carboxylic acid derivatives".
Chemical Abstracts, vol. 101, No. 11, Sep. 10, 1994, Ohio, p. 631, abstract of Schurnal Organitscheskoi Chimii, vol. 20 No. 3, Mar. 1984 pp. 577–583.

Primary Examiner—Johann Richter
Assistant Examiner—Laura R. Cross
Attorney, Agent, or Firm—Edith A. Rice

[57] ABSTRACT

A method of synthesizing a compound having a 1,3-thiazolidin-4-one ring appended at the 2-position by a double bond to the active methylene position of a ketomethylene or malononitrile moiety, which comprises reacting the corresponding ketomethylene compound or malononitrile with an isothiocyanate in the presence of a base, reacting the resulting product with a haloacetic acid or haloacetic ester, followed by eliminating water or alcohol to form the 1,3-thiazolidin-4-one ring. A fragment necessary to complete a merocyanine, oxonol, hemicyanine, benzylidene, cinnamylidene or holopolar cyanine dye can be appended to the 1,3-thiazolidin-4-one ring to obtain the desired dye.

6 Claims, No Drawings

METHOD OF SYNTHESIZING DYES AND PRECURSOR COMPOUNDS THEREFOR

This is a continuation-In-Part of application Ser. No. 08/395,265 filed Feb. 28, 1995, now abandoned.

FIELD OF THE INVENTION

This invention relates to a method of preparing precursor compounds which can be used to prepare sensitizing dye compounds, as well as a method of preparing such sensitizing dye compounds.

BACKGROUND

Complex non-ionic tri-nuclear dyes derived from merocyanines, which may be conveniently described as a class of complex merocyanines, are well known. Such dyes are described in some detail by Hamer in *The Cyanine Dyes and Related Compounds*, Interscience Publishers, New York, 1964, pages 672–674, and by Brooker in *The Theory of the Photographic Process*, T. H. James, editor, 3rd Edition, MacMillan, New York, 1966, pages 221–223. When substituted with water solubilizing groups, certain dyes of this class are useful as low staining sensitizing dyes for silver halide photographic emulsion, in particular for graphic arts applications. For example, in U.S. Pat. No. 5,116,722 and EP 0 540 295, dyes of the formula (i) are described as efficient, low staining sensitizers for the red spectral region.

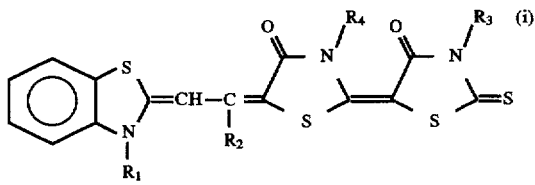

(i)

wherein two or more of $R_1$–$R_4$ represent water solubilizing groups.

The usual method for the synthesis of complex merocyanines of the above type involves S-alkylation of the corresponding merocyanine, followed by displacement of the alkylthio group in the alkylated dye by a rhodanine, as shown in the following scheme.

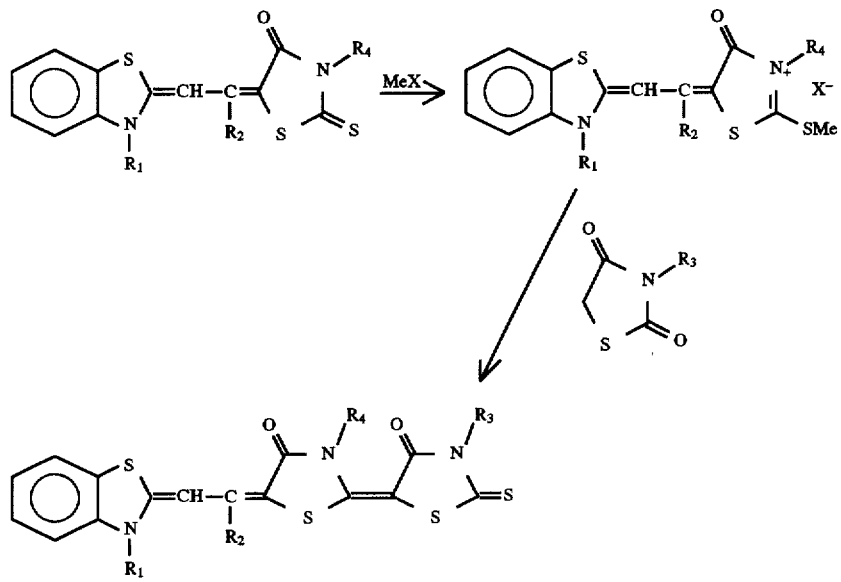

Similar treatment of merocyanines in which the two methine groups of the polymethine chain are replaced by a double bond yields the corresponding complex merocyanines.

In the second step of the above synthesis, the rhodanine nucleus may be replaced by other cyclic or acyclic ketomethylene compounds commonly used in the synthesis of merocyanines. If, for example, malononitrile is used, dyes corresponding to formula (ii) are obtained:

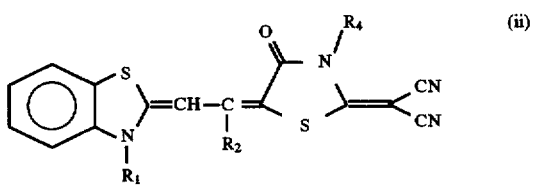

(ii)

The synthetic method described above often gives low yields and is inconvenient, in that a merocyanine dye must first be synthesized as the starting material for the synthesis.

Tetra-nuclear merocyanines of formula (iii) below are described in UK 489,335 and were synthesized in a manner analogous to that described above for tri-nuclear merocyanines, by using a tri-nuclear merocyanine as starting material:

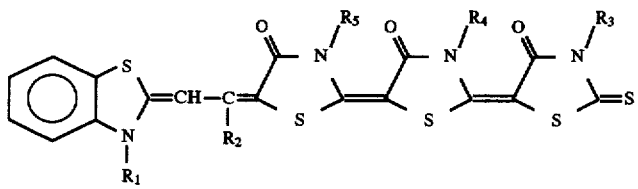

Merocyanine dyes of formula (iii), however, have received less interest than dyes of formula (i), probably as a result of the poor yields and low purity of dyes obtained by using the foregoing synthetic procedure. This increase in synthetic difficulty with each additional nucleus is remarked by Brooker in the text of *The Theory of the Photographic Process*, 3rd Edition, cited above.

It would be desirable then to have a method of synthesizing merocyanine dyes such as those of formula (i), (ii) or (iii), which was relatively simple to perform and provides good yields of dye.

SUMMARY OF THE INVENTION

Accordingly, the present invention provides a method of synthesizing a compound having a 1,3-thiazolidin-4-one ring appended at the 2-position by a double bond to the active methylene position of a ketomethylene or malononitrile moiety, the method comprising reacting the corresponding ketomethylene compound or malononitrile with an isothiocyanate in the presence of a base, reacting the resulting product with a haloacetic acid or haloacetic ester, followed by eliminating water or alcohol to form the 1,3-thiazolidin-4-one ring.

The present invention also provides a method of forming a dye, using as a starting material a compound having a 1,3-thiazolidin-4-one ring appended at the 2-position by a double bond to the active methylene position of a ketomethylene or malononitrile moiety, the method comprising appending to the 5-position of the 1,3-thiazolidin-4-one ring a fragment necessary to complete a merocyanine, oxonol, hemicyanine, benzylidene, cinnamylidene or holopolar cyanine dye. The foregoing dye classes are described in *The Theory of the Photographic Process*, 3rd Edition cited above, pages 216–226, and *Theory of the Photographic Process*, 4th Edition, T. H. James, MacMillan, New York, 1977, page 198.

The method of the present invention both provides a simple and efficient method of forming the dye precursors described, as well as forming photographic sensitizing dyes from such precursors.

EMBODIMENTS OF THE INVENTION

It will be understood throughout this application that formulae shown for any dyes or precursor compounds of the present invention are to be interpreted as including all stereoisomers where possible. This is particularly true of isomers about a double bond. Thus, considering the following formulae:

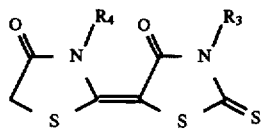

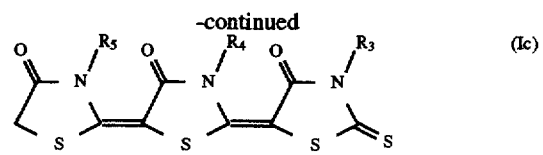

It will be understood that the above formulae, as written, will, for example, respectively include stereoisomers such as structures:

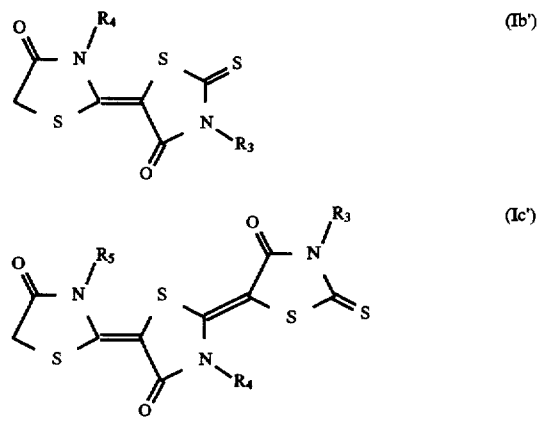

In the present application, reference to any chemical "group" (such as alkyl group, aryl group, heteroaryl group, and the like) includes the possibility of it being both substituted or unsubstituted (for example, alkyl group and aryl group include substituted and unsubstituted alkyl and substituted and unsubstituted aryl, respectively).

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, and the like. Generally, the above groups and substituents thereof may include those having up to 48 carbon atoms, typically 1 to 36 carbon atoms and usually less than 24 carbon atoms (or no more than 20, 12 or even 6 atoms), but greater numbers are possible depending on the particular substituents selected.

It will also be understood throughout this application that reference to a compound of a particular general formula includes those compounds of other more specific formula which specific formula falls within the general formula definition.

By the "active methylene position" of a ketomethylene compound is meant the methylene carbon adjacent to the carbonyl carbon.

The method of the present invention can use as the starting material a compound of formula (I):

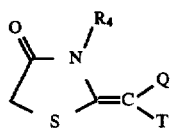
(I)

wherein: $R_4$ is an alkyl, aryl or heterocyclyl group; Q and T may both be —CN, or Q and T are, independently, —CN, —$CO_2R_7$, —$CONR_8R_9$, —$SOR_{10}$, —$SO_2R_{11}$, —$SO_2NR_{12}R_{13}$, wherein $R_7$ through $R_{13}$ are independently alkyl, aryl or heterocyclyl, or Q and T together form a 4 to 7 atom carbocyclic or heterocyclic ring.

Suitable bases for carrying out the reaction of the ketomethylene or malononitrile with the isothiocyanate, are any base which is sufficiently strong to remove a proton from their methylene group, which then facilitates the attack of the carbon of the isothiocyanate group. Typically, such a base will have a pKa of at least 10, more preferably 12 (and most preferably 13). Preferred bases are organic bases such amidine compounds, such as 1,8-diazabicyclo[5.4.0] undec-7-ene ("DBU"), 1,5-diazabicyclo[4.3.0] non-5-ene ("DBN"), or 1,1,3,3,-tetramethylguanidine.

The step in which the water or alcohol is eliminated to form the 1,3-thiazolidin-4-one ring, may occur spontaneously or not depending upon the exact compound being sythesized. In the case where elimination and ring closure does not occur spontaneously or sufficiently fast, this can be aided by heating above room temperature (that is, heating above 20° C., preferably up to about 100° C. or about 120° C., or even higher provided no decomposition of reagents or product occurs), as well as with the presence of an acid (for example, a sulfonic acid such as p-toluene sulfonic acid). All steps of the present method may be performed in any suitable solvent. Preferably, the solvent is an aprotic, polar solvent which of course, is itself subtantially inert to any of the reactants particlularly the isothiocyanate. Examples of suitable solvents include acetonitrile or other alkylnitrile solvents, N,N-dimethylformamide, N,N-dimethylacetamide and dimethylsulfoxide. In some cases an alcohol solvent (which is a protic solvent) may be suitable. However, an aprotic solvent is not necessary for the final step involving elimination of alcohol or water. For this final step, sometimes no solvent may be necessary, or a solvent such acetic acid may be suitable.

The method of the present invention may particularly use malononitrile or a cyclic ketomethylene as the starting material. In such case the method can be represented as a method of synthesizing a compound of formula (Ia):

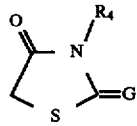
(Ia)

wherein $R_4$ is an alkyl, aryl or heterocyclic group, and G represents a ketomethylene or malononitrile group as shown below:

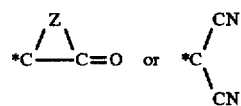

where * is the point of attachment of G as shown in formula (Ia), and Z represents the atoms necessary to complete a subsituted or unsubstituted 4 to 7-membered (preferably 5 or 6) alicyclic or heterocyclic ring. The method in such case comprises reacting

or $H_2C(CN)_2$ with an isothiocyanate of formula (II) in the presence of a base to obtain a compound of formula (III):

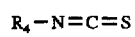
(II)

(III)

where $R_4$ is an alkyl, aryl or heterocyclic group. Compound (III) is then reacted with a haloacetic acid or a haloacetic ester of formula $XCH_2CO_2R_6$, wherein X is a halogen and $R_6$ is H, alkyl group or aryl group, to obtain compound (IV):

(IV)

and then $HOR_6$ is eliminated to form compound (Ia).

Since Z can complete a substituted ring as defined, formula (Ia) in turn includes structures of the formula below:

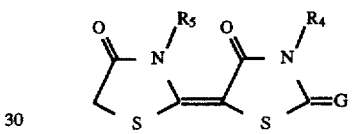

wherein $R_4$ and $R_5$ are, independently, an alkyl, aryl or heterocyclic group.

The compound of formula (Ia) which the method of the present invention may be used to make, may particularly be of formula (Ib) below:

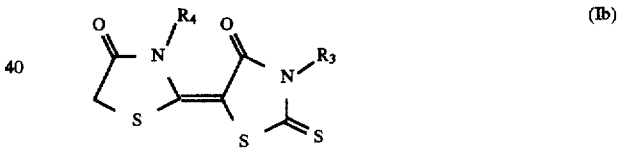
(Ib)

In this case, the isothiocyanate of formula (II) is reacted with a compound of formula:

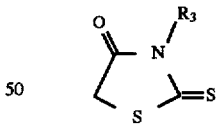

in the presence of a base to obtain a compound of formula (IIIa):

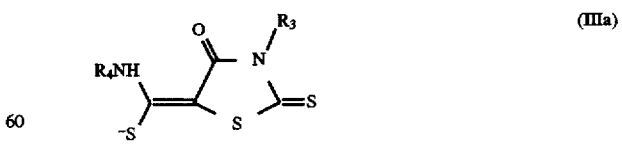
(IIIa)

where $R_3$ is an alkyl, aryl or heterocyclic group. This again is followed by reaction with haloacetic acid or haloacetic ester and water or alcohol elimination as already described.

It will be appreciated that in the same manner as the foreoing, a 1,3-thiazolidin-4-one ring can be added to a starting ketomethylene reagent having two rings. For example, the compound of formula (Ib) may be the starting ketomethylene in which case the product would be a compound of the formula (Ic):

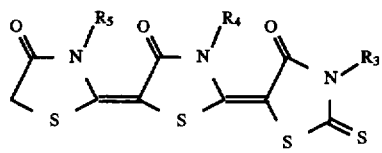
(Ic)

where R$_5$ is an alkyl, aryl or heterocyclic group.

It will also be appreciated by specifically using malononitrile instead of a ketomethylene, a compound of formula (Id) can be obtained:

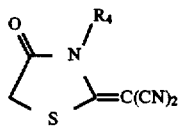
(Id)

It will be appreciated that precursors of the type of the present invention can be used to synthesize dyes in the manner described above. The details of the method in which the 5-position carbon of the 1,3-thiazolidin-4-one ring is appended to a fragment necessary to complete a merocyanine, oxonol, hemicyanine, benzylidene, cinnamylidene or holopolar cyanine dye, are essentially carried out in the same manner in which a single ring, such as a rhodanine ring, is appended to the necessary fragment to form a dye. Syntheses of the foregoing type are described in detail in Hamer in *The Cyanine Dyes and Related Compounds*, Interscience Publishers, New York, 1964, and by Brooker in *The Theory of the Photographic Process*, T. H. James, editor, 3rd Edition, MacMillan, New York, 1966. The foregoing references, and all other references cited herein are incorporated in the present application by reference.

Examples of acid nuclei to which the methine chain can be linked, include rhodanine, thiohydantoin, hydantoin, thiobarbituric acid, barbituric acid, pyrazolinone, 2,2-dialkyl-1,3-dioxane-4,6-dione (where the alkyls are typically methyl), cyclohexane-1,3-dione, pyrazolidine dione.

Examples of basic nuclei to which the methine chain can be linked, include oxazole, imidazole, thiazole, selenazole, benzoxazole, benzimidazole, benzothiazole, benzoselenazole, naphthoxazole, naphthimidazole, naphthothiazole, naphthoselenazole, thiazoline, 1,3,4-thiadiazole group.

The method of the present invention for synthesizing a dye using 1,3-thiazolidin-4-one ring compounds synthesized by the inventive method, may particularly be used to append the 5-position carbon atom of a heterocyclic ring of formula (I) (which, of course, includes the more specific formula (Ia), (Ib), Ic), and (Id)), defined above, to a methine which is linked to an acidic or basic nucleus.

When the method of the present invention is used to synthesize a merocyanine dye of formula (V) below, it can be represented by the sequence below:

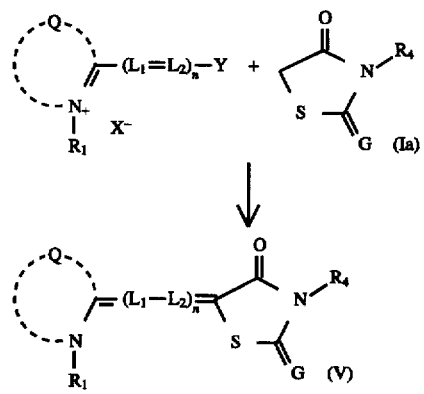

wherein: Q represents the atoms necessary to complete a substituted or unsubstituted 5- or 6-membered alicyclic or heterocyclic ring; each L is a methine group; Y is a leaving group; X$^-$ is an anion as may be needed to balance the charge on the molecule shown; R$_1$ is an alkyl, aryl or heterocyclic group; and R$_4$ and G are defined above in connection with formula (I). Examples of Y include an alkoxy or alkylthio (either particularly of 1 to 20, 1 to 10, or 1 to 6 carbon atoms), acetanilido or arylthio group (either particularly of 6 to 20, or 6 to 12 carbon atoms), or halogen (particularly chloro).

It will be appreciated that since G may be a substituted ring, dyes of formula (V) can include dyes of formula (Va) below:

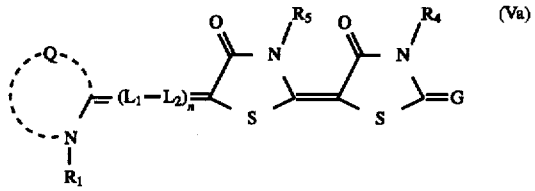
(Va)

In the method of the foregoing sequence, the starting compound (Ia) may, for example, be (Ib) or (Ic):

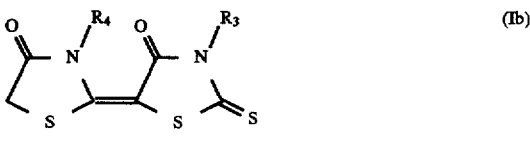
(Ib)

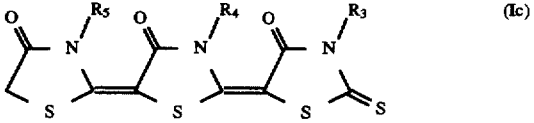
(Ic)

wherein: R$_4$ and R$_5$ are, independently, an alkyl, aryl or heterocyclic group. It will be appreciated though, that other suitable compounds of formula (Ia) (or of formula (I)) can be used in an analogous manner. For example, compound (Ia) could be a compound analogous to (Ib) and (Ic) but with four, five, or more 1,3-thiazolidin-4-one rings (an end one being a rhodanine ring).

To produce low-staining dyes, including complex merocyanine sensitizing dyes, it is often desirable to provide the dye with one or more water water solubilizing groups. Particularly useful as water solubilizing groups are carboxyalkyl and/or sulfoalkyl substituents. Any compounds of formulae (i) (including formula (Ia)) which contain N-carboxyalkyl substituents are advantageously synthesized with the carboxyl function protected as an ester. It is convenient to cleave the ester to a carboxylic acid, or a salt thereof, either before or after dye formation. This is preferably done by acid hydrolysis (since basic hydrolysis tends to induce decomposition of intermediates or dyes). The hydrolysis can be carried out typically between about 20° C. to about 100° C. The optimum time and temperature for hydrolysis of each compound may vary (the optimum conditions being the best compromis between rapid hydrolysis and minimum decomposition). The acid may for example be aqueous HCl (for example, 20–30% by weight of HCl). In some cases the dye or intermediate may be insufficiently soluble in this medium and a co-solvent may be required. Trifluoracetic acid has been found to be particularly useful as a co-solvent.

All heterocyclic and aromatic groups described above, may particularly have from 6 to 20, or form 6 to 15, C atoms. Heterocyclic groups may particularly have from 4 to 7 (or 5 or 6) carbon atoms, with 1 to 4 heteroatoms selected from O, N, S or Si. Examples of aryl include phenyl, tolyl, and the like, any of which may be substituted or unsubstituted. All alkyl or alkoxy groups described above may particularly have from 1 to 20 carbon atoms, or even from 1 to 8 carbon atoms. Examples of alkyl include methyl, ethyl, propyl, and the like, and substituted alkyl groups (preferably a substituted lower alkyl containing from 1 to 8 carbon atoms) such as hydroxyalkyl group (for example, 2-hydroxyethyl), a sulfoalkyl group, (for example, 4-sulfobutyl, 3-sulfopropyl) and the like. Water solubilizing groups on dyes made by the present invention have been described above and can additionally include an acylsulfonamido group such as —CH$_2$—CO—NH—SO$_2$—CH$_3$. Thus, dyes made by the method of the present invention may have one or more substituents such as 3-sulfobutyl, 3-sulfopropyl or 2-sulfoethyl and the like.

Substituents on any of the specified substituent groups defined above, can include halogen (for example, chloro, fluoro, bromo), alkoxy (particularly 1 to 10 carbon atoms; for example, methoxy, ethoxy), substituted or unsubstituted alkyl (particularly of 1 to 10 carbon atoms, for example, methyl, trifluoromethyl), amides (particularly of 1 to 10 or 1 to 6 carbon atoms), alkoxycarbonyl (particularly of 1 to 10 or 1 to 6 carbon atoms), and other known substituents, and substituted and unsubstituted aryl ((particularly of 1 to 10 or 1 to 6 carbon atoms) for example, phenyl, 5-chlorophenyl), thioalkyl (for example, methylthio or ethylthio), hydroxy or alkenyl (particularly of 1 to 10 or 1 to 6 carbon atoms) and others known in the art. Additionally, any of the substituents may optionally be non-aromatic.

The following compounds can be made in accordance with this invention.

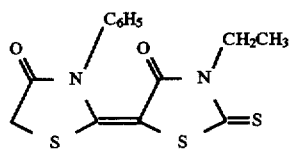

I-1

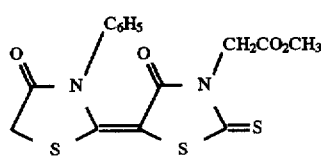

I-2

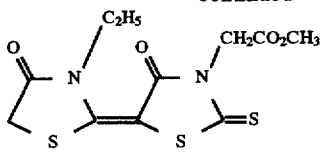

I-3

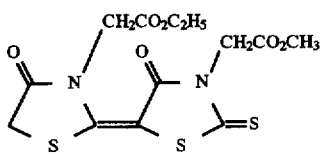

I-4

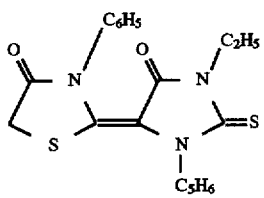

I-5

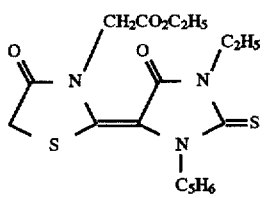

I-6

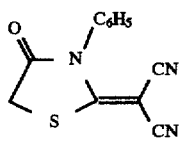

I-7

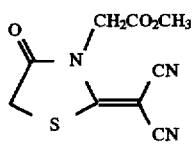

I-8

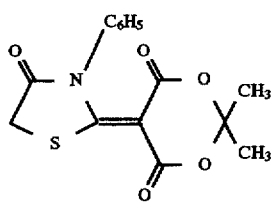

I-9

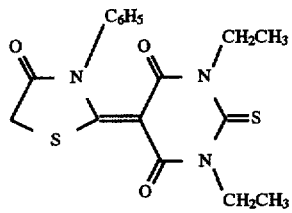

I-10

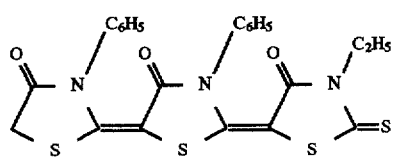

I-11

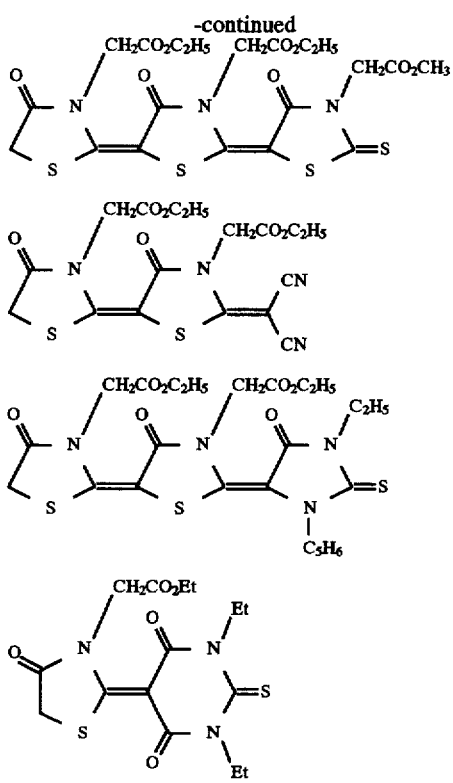

Dyes made by the method of the present invention have application particularly as sensitizing dyes (and particularly as red sensitizing dyes) in silver halide photographic elements.

Such photographic elements will typically have at least one light sensitive silver halide emulsion layer and a support. They can be single color elements or multicolor elements, but are preferably black and white elements for use in graphic arts applications. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler.

The element can contain additional layers, such as filter layers, interlayers, overcoat layers, subbing layers, and the like. All of these can be coated on a support which can be transparent or reflective (for example, a paper support).

Photographic elements may also usefully include a magnetic recording material as described in Research Disclosure, Item 34390, November 1992, or a transparent magnetic recording layer such as a layer containing magnetic particles on the underside of a transparent support as in U.S. Pat. No. 4,279,945 and U.S. Pat. No. 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, with the reverse order on a reflective support being typical.

Such photographic elements can be used in conventional cameras including what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed. However, photographic elements containing the dyes synthesized by the method of the present invention are preferably used as sensitizers for graphic arts (black and white) films.

In the following discussion of suitable materials for use in photographic elements, reference will be made to Research Disclosure, September 1994, Number 365, Item 36544, published by Kenneth Mason Publications, Ltd., Dudley Annex, 12a North Street, Emsworth, Hampshire PO10 7DQ, ENGLAND, which will be identified hereafter by the term "Research Disclosure I." The Sections hereafter referred to are Sections of the Research Disclosure I.

The silver halide emulsions employed in the photographic elements may be negative-working, such as surface-sensitive emulsions or unfogged internal latent image forming emulsions, or positive working emulsions of internal latent image forming emulsions (that are either fogged in the element or fogged during processing). Suitable emulsions and their preparation as well as methods of chemical and spectral sensitization are described in Sections I through V. Color materials and development modifiers are described in Sections V through XX. Vehicles which can be used in the photographic elements are described in Section II, and various additives such as brighteners, antifoggants, stabilizers, light absorbing and scattering materials, hardeners, coating aids, plasticizers, lubricants and matting agents are described, for example, in Sections VI through X and XI through XIV. Manufacturing methods are described in all of the sections, other layers in Sections XI and XIV, processing methods and agents in Sections XIX and XX, and exposure alternatives in Section XVI.

Supports for the photographic elements include polymeric films such as cellulose esters (for example, cellulose triacetate and diacetate) and polyesters of dibasic aromatic carboxylic acids with divalent alcohols (for example, poly (ethyleneterephthalate), poly(ethylene-napthalates)), paper and polymer coated paper. Such supports are described in further detail in Research Disclosure I, Section XV.

The photographic elements may also contain materials that accelerate or otherwise modify the processing steps of bleaching or fixing to improve the quality of the image. Bleach accelerators described in EP 193,389; EP 301,477; U.S. Pat. No. 4,163,669; U.S. Pat. No. 4,865,956; and U.S. Pat. No. 4,923,784 are particularly useful. Also contemplated is the use of nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the couplers may be blocked or coated in protected form as described, for example, in Japanese Application 61/258,249 or U.S. Pat. No. 5,019,492.

The photographic elements may further contain other image-modifying compounds such as "Developer Inhibitor-Releasing" compounds (DIR's). DIR compounds are disclosed, for example, in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. DIRs that have particularl application in color reversal elements are disclosed in allowed U.S. patent applications Ser. Nos. 08/004,019, 08/005,319, 08/005,472, and 08/007,440.

The emulsions and materials to form the photographic elements may be coated on pH adjusted support as described in U.S. Pat. No. 4,917,994; with epoxy solvents (EP 0 164 961); with additional stabilizers (as described, for example, in U.S. Pat. No. 4,346,165; U.S. Pat. No. 4,540,653 and U.S. Pat. No. 4,906,559); with ballasted chelating agents such as those in U.S. Pat. No. 4,994,359 to reduce sensitivity to polyvalent cations such as calcium; and with stain reducing compounds such as described in U.S. Pat. No. 5,068,171 and U.S. Pat. No. 5,096,805. Other compounds useful in the above described photographic elements are disclosed in Japanese Published Applications 83-09,959; 83-62,586; 90-072,629, 90-072,630; 90-072,632; 90-072,633; 90-072, 634; 90-077,822; 90-078,229; 90-078,230; 90-079,336; 90-079,338; 90-079,690; 90-079,691; 90-080,487; 90-080, 489; 90-080,490; 90-080,491; 90-080,492; 90-080,494; 90-085,928; 90-086,669; 90-086,670; 90-087,361; 90-087, 362; 90-087,363; 90-087,364; 90-088,096; 90-088,097; 90-093,662; 90-093,663; 90-093,664; 90-093,665; 90-093, 666; 90-093,668; 90-094,055; 90-094,056; 90-101,937; 90-103,409; 90-151,577.

The silver halide used in the photographic elements may be silver iodobromide, silver bromide, silver chloride, silver chlorobromide, silver chloroiodobromide, and the like.

The type of silver halide grains preferably include polymorphic, cubic, and octahedral. The grain size of the silver halide may have any distribution known to be useful in photographic compositions, and may be ether poly-dipersed or monodispersed. Tabular grain silver halide emulsions may also be used. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: *Research Disclosure*, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The silver halide grains may be prepared according to methods known in the art, such as those described in *Research Disclosure I* and James, *The Theory of the Photographic Process*. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in *Research Disclosure I* and the references cited therein.

The photographic elements, as is typical, provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, ruthenium, rhodium, phosphorous, or combinations thereof. Chemical sensitization is generally carried out at pAg levels of from 5 to 10, pH levels of from 5 to 8, and temperatures of from 30° to 80° C., as illustrated in *Research Disclosure*, June 1975, item 13452 and U.S. Pat. No. 3,772,031.

The sensitizing dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

The photographic elements can be imagewise exposed using any of the known techniques, including those described in *Research Disclosure I*, section XVI. This typically involves exposure to light in the visible region of the spectrum, and typically such exposure is of a real image through a lens. However, exposure may be by exposure to a computer stored or generated image by means of light emitting devices (such as light controlled by light valves, CRT and the like). The photographic elements can be processed by any known process.

The method of the present invention will be further described in the examples below.

EXAMPLE 1. SYNTHESIS OF COMPOUND I-1

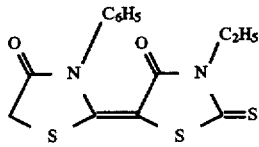

Step 1: A solution of 3-ethylrhodanine (8.1 g, 0.05 mol) and phenyl isothiocyanate (6.8 g, 0.05 mol) in acetonitrile (50 mL) was stirred as 1,8-diazabicyclo [5.4.0]undec-7-ene (DBU, 7.6 g, 0.05 mol) was added, in portions, in 5 min. The mixture was stirred for 2 hr, as some solid separated, then slowly diluted with ether (300 mL). The solid was collected, washed with ether and dried overnight at room temperature. The yield of compound having the following structure was 13.5 g:

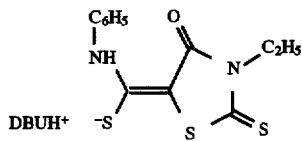

Step 2: To 9.0 g (0.02 mol) of this compound was added ethyl bromoacetate (5.0 g, (0.03 mol) and a mild evolution of heat occurred. The mixture heated at 100° C. for 30 min. The resulting solid was well slurried in methanol (50 mL), then collected and washed with methanol. The yield of I-1 was 6.2 g.

EXAMPLE 2. SYNTHESIS OF COMPOUND I-9

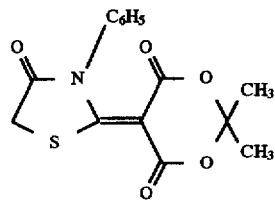

To a stirred solution of 2,2-dimethyl-1,3-dioxane-4,6-dione (1.44 g, 0.01 mol) and phenyl isothiocyanate (1.35 g, 0.01 mol) in acetonitrile (10 mL) was added DBU (1.52 g, 0.01 mol) in one portion. After 1 hr, ethyl bromoacetate (2.5 g, 0.015 mol) was added. Solvent was evaporated and the residue heated at 100° C. for 2.5 hr. After cooling, the solid mass was stirred with methanol (10 mL). The solid was collected and washed with methanol. The yield of compound I-9 was 0.93 g.

EXAMPLE 3. SYNTHESIS OF COMPOUND I-4

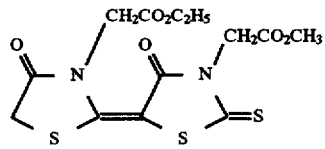

To a stirred solution of N-methoxycarbonylmethylrhodanine (41 g, 0.2 mol) and ethoxycarbonylmethyl isothiocyanate (29 g, 0.2 mol) in acetonitrile (200 mL), DBU (30.4 g, 0.2 mol) was added, dropwise. After a further 45 min, ethyl bromoacetate (66.8 g, 0.4 mol) was added and the solution became warm. Solvent was evaporated and the residue was heated at 100° C. for 2 hr. After cooling to room temperature, ethanol (50 mL) was added and the mixture well stirred. Solid was collected and washed with ethanol, then with ligroin. The yield of I-4 was 38.2 g.

EXAMPLE 4 SYNTHESIS OF COMPOUND I-11

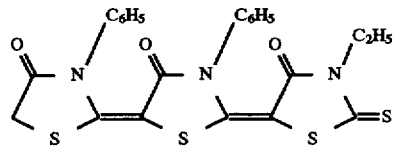

Step 1: A suspension of compound I-1 (0.67 g, 0.002 mol) in acetonitrile (5 mL) and phenyl isothiocyanate (0.27 g, 0.002 mol) was stirred as a solution of DBU (0.3 g, 0.002 mol) in acetonitrile (2 mL) was added in about 30 sec. Solids partially dissolved then a new solid began to separate. After stirring for a further 5 min, the solid was collected and washed with acetonitrile. The yield of compound having the following structure was 1.1 g.

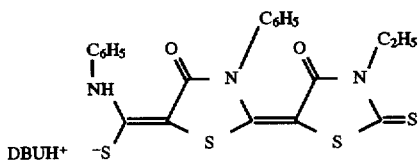

Step 2: 0.62 g, 0.001 mol of the above compound was treated with ethyl bromoacetate (0.33 mol, 0.002 mol) and heated at 100° C. for 30 min. After stirring in methanol (5 mL), the solid was collected and washed with more of the same solvent. The yield of compound I-11 was 0.46 g.

EXAMPLE 5. SYNTHESIS OF COMPOUND I-12

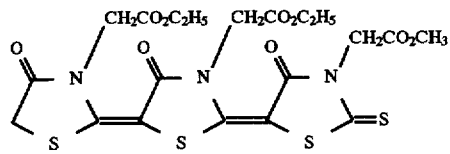

A solution of Compound I-4 (15.6 g, 0.04 mol) and ethoxycarbonylmethyl isothiocyanate (6.4 g, 0.04 mol) in acetonitrile (100 mL) was stirred as DBU (6.6 g, 0.04 mol) was slowly added and stirring continued for 30 min. Ethyl bromo acetate (6.7 g, 0.04 mol) was then added. After a further 30 min, acetic acid (25 mL) was added and the mixture heated at reflux for 2 hr. After cooling, the solid was collected and washed with acetonitrile, then with ligroin. The yield of I-12 was 12.0 g.

EXAMPLE 6. SYNTHESIS OF DYE V-1

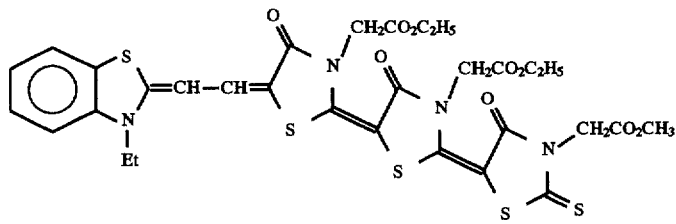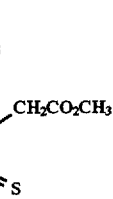

To a well stirred suspension of Compound I-12 (0.90 g, 0.002 mol) and 2-β-acetanilidovinyl-3-ethylbenzothiazolium iodide (1.15 g, 0.002 mol) in acetonitrile (20 mL) was added triethylamine 0.4 g, 0.004 mol) in one portion. The solids dissolved, then dye began to precipitate almost immediately. After stirring for 30 min, the dye was collected and washed with acetonitrile. The yield of V-1 was 1.0 g.

EXAMPLE 7. SYNTHESIS OF DYE V-2

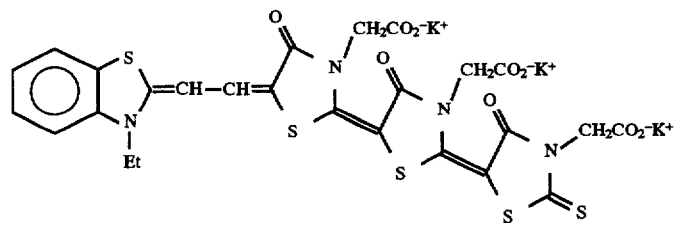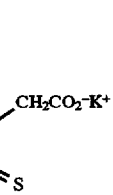

2 g of the dye of Example 6 was heated at reflux in a mixture of conc HCl (25 mL) and trifluoroacetic acid (20 mL) for 1 hr. After cooling, the solution was slowly added to ice-water (350 mL). The finely divided dye which separated was collected and well washed with water. This dye was then added to a solution of potassium acetate (4 g) in methanol (100 mL) and the mixture heated at the boiling point for 5 min, then stirred at room temperature for 2 hr. The yield of V-2 was 1.97 g. λmax (90% methanol) 593 nm, $\epsilon_{max}$ 13.5×10$^4$.

EXAMPLE 8. SYNTHESIS OF DYE V-3

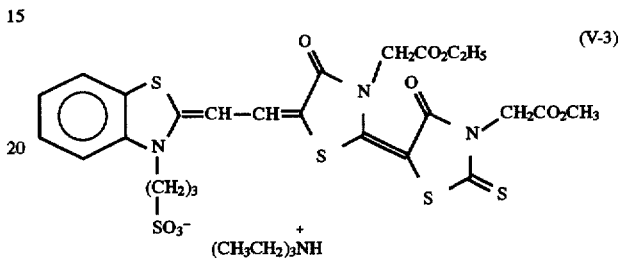

To Compound I-4 (0.93 g, 0.0024 mol) and anhydro-2-β-acetanilidovinyl-3-(3-sulfopropyl)benzothiazolium hydroxide (1.00 g, 0.0024 mol) suspended in acetonitrile (5 mL) was added triethylamine (0.48 g, 0.0048 mol). The mixture was heated to boiling, as all the solids dissolved. 20 mL more acetonitrile was added. Upon cooling, the dye crystallized. It was collected and washed with acetonitrile. The yield was 1.12 g.

EXAMPLE 9. SYNTHESIS OF DYE V-4

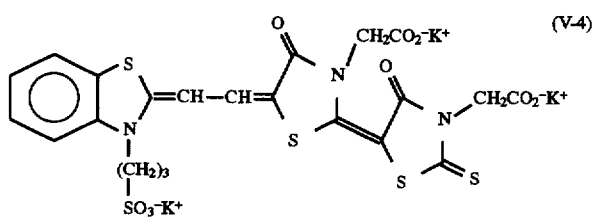

Dye IV-3 was hydrolysed by the method described in Example 7, to obtain V-4, λmax (90% methanol) 568 nm. $\epsilon_{max}$ 10.1×10$^4$.

EXAMPLE 10—PREPARATION OF COMPOUND I-15

A mixture of 1,3-diethyl-2-thiobarbituric acid (20.0 g), DBU (15.2 g) and acetonitrile (100 mL) was stirred at room temperature until a clear solution was obtained. Ethoxycarbonylmethyl isothiocyanate (14.5 g) was added and the mixture heated at reflux temperature for 15 minutes. After cooling the mixture to room temperature, ethyl bromoacetate (1.45 g) was added. After a further 15 minutes, ice and water were slowly added to give a total volume of about 500 mL. The solid which precipitated was collected and washed with water. After drying, the yield was 34.8 g (81%). nmr (DMSO-d6) was consistent with the structure below:

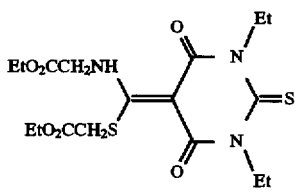

A mixture of the foregoing compound (30 g) and p-toluenesulfonic acid monohydrate (3 g) was heated in an oil bath at 100° C. for 40 min. Methanol (200 mL) was added cautiously to the hot mixture and the resulting solution cooled to room temperature. The solid which separated was collected and washed with methanol. After drying, the yield was 19.5 g (73%). nmr (DMSO-d6) was consistent with the structure of (I-15) below:

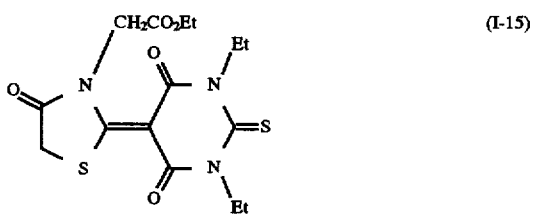

The preceding examples are set forth to illustrate specific embodiments of this invention and are not intended to limit the scope of the compositions or materials of the invention. It will be understood that variations and modifications can be effected within the spirit and scope of the invention.

I claim:

1. A method of synthesizing a compound having a 1,3-thiazolidin-4-one ring appended at the 2-position by a double bond to the active methylene position of a cyclic ketomethylene moiety, the method comprising reacting the corresponding cyclic ketomethylene compound with an isothiocyanate in the presence of a base, reacting the resulting product with a haloacetic acid or haloacetic ester, followed by eliminating water or alcohol to form the 1,3-thiazolidin-4-one ring.

2. A method of synthesizing a compound of formula (Ia):

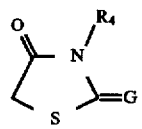

wherein R$_4$ is an alkyl, aryl or heterocyclic group, and G represents a cyclic ketomethylene group as shown below:

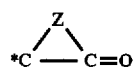

where * is the point of attachment of G to the ring shown in formula (Ia), and Z represents the atoms necessary to complete a substituted or unsubstituted 4 to 7 membered alicyclic or heterocyclic ring;

the method comprising:

reacting

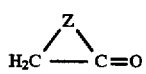

with an isothiocyanate of formula (II) in the presence of a base to obtain a compound of formula (III):

 (II)

 (III)

where R$_4$ is an alkyl, aryl or heterocyclic group;

reacting compound (III) with a haloacetic ester or haloacetic acid of the formula XCH$_2$CO$_2$R$_6$ to obtain a compound of formula (IV):

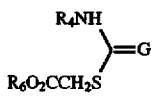 (IV)

and eliminating HOR$_6$ to form compound (Ia);

wherein X is a halogen and R$_6$ is H, alkyl group or aryl group.

3. A method according to claim 2, wherein following the reaction of compound (III) with the haloacetic ester or haloacetic acid, the resulting compound is heated under acidic conditions to eliminate HOR$_6$ and form compound (Ia).

4. A method according to claim 3 wherein the acid used to provide the acidic conditions is an organic sulfonic acid.

5. A method according to claim 2 wherein the base is an organic base having a pKa of at least 12.

6. A method according to claim 2 wherein the reactions with isothiocyanate and haloacetic acid or ester, are performed in a polar, aprotic solvent.

* * * * *